United States Patent [19]

Hoeks et al.

[11] Patent Number: 5,151,351
[45] Date of Patent: Sep. 29, 1992

[54] PROCESS FOR THE PRODUCTION OF 6-HYDROXYNICOTINIC ACID

[75] Inventors: Frans Hoeks, Naters; Daniel Venetz, Brig, both of Switzerland

[73] Assignee: Lonza Ltd., Gampel/Valais, Switzerland

[21] Appl. No.: 705,659

[22] Filed: May 24, 1991

Related U.S. Application Data

[63] Continuation of Ser. No. 629,673, Dec. 18, 1992.

[30] Foreign Application Priority Data

Dec. 20, 1989 [CH] Switzerland ............... 4555/89

[51] Int. Cl.$^5$ .............. C12P 17/12; C12R 1/40; C12R 1/025; C12R 1/07
[52] U.S. Cl. .................. 435/122; 435/121; 435/824; 435/877
[58] Field of Search ............ 435/121, 122, 824, 877

[56] References Cited

U.S. PATENT DOCUMENTS 4,038,993  4/1977  Geiss et al. ............. 131/141
4,738,924  4/1988  Kulla et al. ............. 435/121

FOREIGN PATENT DOCUMENTS 644847  8/1984  Switzerland .
658866  12/1986  Switzerland .
658867  12/1986  Switzerland .
664374  2/1988  Switzerland .

OTHER PUBLICATIONS

Briaucourt et al., J. Chim. Ther. (1973), 8 (2), 226 to 232.
Allison, JJC, J. Biol. Chem. (1943), 147, 785.
Behrman, E. J., et al., J. Biol. Chem. 228 (1957), 923.
Hunt, A. L., Biochem. J. 91958), 72, pp. 1 to 7.
Ensign and Rittenberg, J. Biol. Chem. 239 (1964), pp. 2285-2291.
Munoz, J., et al., J. Bact., 57, (1949), 269-278.
Haynes, W. C., J. Bact., 81, (1961), 385-386.
Bartholomew, J. W., J. Gen. Microbiol., 3, (1949), 340-349.
Lockwood, L. B., et al., J. Bact., 42, (1941), 51-61.
Kogut, M., et al., Biochem. J., 55, 91953), 800-811.
*The National Collection of Industrial Bacteria*, Catalogue of Strains, 3rd Ed., England, 174, 177 and 178.

Primary Examiner—Herbert J. Lilling
Attorney, Agent, or Firm—Fisher, Christen & Sabol

[57] ABSTRACT

A process for the production of 6-hydroxynicotinic acid from nicotinic acid by means of enzymatic hydroxylation in the presence of microorganisms of the genera Pseudomonas, Bacillus or Achromobacter. By maintaining a specific concentration range during the addition of nicotinic acid, the biomass formation can take place in the same process step as the product formation, without product losses occurring by further decomposition.

4 Claims, No Drawings

PROCESS FOR THE PRODUCTION OF 6-HYDROXYNICOTINIC ACID

This is a continuation of application Ser. No. 629,673 filed on Dec 18, 1990 of Frans Hoeks and Daniel Venetz.

BACKGROUND OF THE INVENTION

1. Field of the Invention

The invention relates to a process for the production of 6-hydroxynicotinic acid by enzymatic hydroxylation of nicotinic acid.

2. Prior Art

Processes are known which make possible the production of 6-hydroxynicotinic acid by means of live microorganisms of the genera Pseudomonas, Bacillus or Achromobacter (see Swiss Patent Nos. 658,866 and 658,867). Such processes use a biomass suspension of the corresponding microorganisms, which are obtained in a separate process step by multiplication of a starter culture. The actual hydroxylation takes place either in a batch process with single addition of nicotinic acid as the sodium salt (batch process, see Swiss Patent No. 658,866), or in a continuous process in which the nicotinic acid is added as the (easily soluble) magnesium or barium salt and the 6-hydroxynicotinic acid is isolated as slightly soluble magnesium or barium salt (see Swiss Patent No. 658,867). Since the multiplication of the microorganisms is inhibited by the nicotinic acid concentrations used in such processes, it is necessary in both processes to obtain the total amount of the effective biomass in an upstream process step. Moreover, the known processes for the enzymatic production of 6-hydroxynicotinic acid have still other drawbacks. The continuous process according to Swiss Patent No. 658,867 yields magnesium or barium salts from which the 6-hydroxynicotinic acid is released by acid addition. In this case, the magnesium or barium salt of the added acid results, which has to be disposed of as waste. But especially soluble barium salts are highly toxic for higher organisms. With prolonged continuous operation, moreover incrustations by the crystallized salts or foreign infections easily occur.

BROAD DESCRIPTION OF THE INVENTION

An object of the invention is to provide a similar process, which yields 6-hydroxynicotinic acid in high concentration and good yield, while the above-mentioned drawbacks of the prior art are avoided. Other objects and advantages of the invention are set out herein or are obvious to one ordinarily skilled in the art.

The objects and advantages of the invention are achieved by the invention process.

The invention involves a process for the production of 6-hydroxynicotinic acid by microbiological hydroxylation of nicotinic acid under aerobic conditions. Nicotinic acid or a soluble salt of nicotinic acid or a solution containing a nicotinic acid is added continuously or by portions to a starter culture of the microorganisms. The nicotinic acid noncentration in the culture during the period of addition is always greater than zero and at least remains substantially below the concentration, above which a growth inhibition of the microorganisms occurs, until the formed 6-hydroxynicotinic acid inhibits further growth, so that the multiplication of the microorganism and the formation of the 6-hydroxynicotinic acid take place in the same process step.

It was found surprisingly that it is possible to get by without the separate obtaining of the biomass, if, starting from a starter culture obtained in a way known in the art, the nicotinic acid is added so that the nicotinic acid concentration in the suspension of microorganisms remains substantially below that concentration, above which the multiplication of the microorganisms is inhibited. The term "substantially" herein means that, if need be, the concentration is exceeded for a short time and/or locally, especially at the addition site before the complete and thorough mixing has taken place. It was to be expected that biomass is formed under these conditions, but it is surprising that during this growth phase 6-hydroxynicotinic acid is produced and is not further metabolized, so that, after completion of the nicotinic acid addition and complete consumption of the nicotinic acid, the 6-hydroxynicotinic acid can be isolated in practically quantitative yield by processes known in the art. The increasing concentration of 6-hydroxynicotinic acid increasing during the addition of nicotinic acid in this case inhibits the cell growth to an increasing extent. But the growth comes to a complete standstill only at relatively high concentrations of 6-hydroxynicotinic acid. Depending on the strain of microorganisms used, these standstill levels are in the range of 50 g/l or above. In a surprising way, then the further decomposition of 6-hydroxynicotinic acid no longer occurs either. But an inhibition of the nicotinic acid hydroxylase is observed only at still higher concentrations and thus limits the attainable product concentration at 100 percent yield. It is essential for the process according to the invention that the nicotinic acid concentration not drop to zero during the cell growth, otherwise the already formed 6hydroxynicotinic acid is decomposed. Only when the maximal concentration of 6-hydroxynicotinic acid is almost reached, is further decomposition also hindered, so that after the end of the nicotinic acid addition its complete consumption can be expected, without yield losses having to be feared to occur. As microorganisms hydroxylating nicotinic acid preferably those of the genera Pseudomonas, Bacillus or Achromobacter are used. In this case, the species *Pseudomonas putida* and *Achromobacter xylosoxydans* are preferred, with the strain *Achromobacter xylosoxydans* DSM 2783 being especially preferred. The preferred microorganisms are described in Swiss Patent No. 658,866 and below. The nicotinic acid concentration in the suspension of microorganisms during the addition period is preferably below 10 g/l. The addition of the nicotinic acid can take place in small portions or continuously, preferably it is a continuous addition.

The nicotinic acid can be added in solid or dissolved form, namely, as free acid or as water-soluble salt, respectively. Preferably the addition is in aqueous solution, especially preferably as an aqueous solution of sodium or potassium salt.

The suspension of microorganisms is suitably aerated and stirred; it is also possible to achieve the necessary stirring action by the blown-in air. The partial pressure of the dissolved oxygen ($pO_2$) in this case advantageously is between 1 mbar and 200 mbars, preferably in the range of 40 to 80 mbars. The use of a mechanical stirrer is preferred. The multiplication of the microorganisms and the formation of the 6-hydroxynicotinic acid preferably take place at a temperature of 20° to 40° C. and a pH of 5.5 to 9.

DETAILED DESCRIPTION OF THE INVENTION

Advantageously other nutrients for the growth of the biomass are used together with the nicotinic acid. These include carbon sources, such as, glycerol or glucose, nitrogen sources, such as, ammonium salts or glutamic acid, as well as mineral salts, trace elements and vitamins. These are suitably used so that their concentration in the microorganisms suspension is neither in the limiting nor in the inhibiting range. But such method is familiar to one skilled in the art. The nutrients can be added individually or in complex form as naturally or artificially produced mixtures. Yeast extract is an especially preferred complex nutrient.

The process according to the invention can also be performed in a continuous mode of operation, by beginning with a separation of the product with simultaneous cell recycling to prevent decomposition to other products, after reaching a concentration of 6-hydroxynicotinic acid, which is high enough. Equipment suitable for this purpose is described, for example, in Swiss Patent No. 664,374. The addition rate of the nicotinic acid in this case is suitably as great as the rate of product removal so that the product concentration remains constant.

The taxonomic description of the new strain *Achromobacter xylosoxydans* DSM 2783 is as follows:
Name: *Achromobacter xylosoxydans* DSM No. 2783
Isolated from: nicotinic acid mother lye

Morphology

Cultivation in nutrient broth (1) cell shape: smale rods 2 to 3.5 u long, approximately 0.6 u wide
(2) arrangement: individually
(3) motility: strongly movable; peritrically flagellated
(4) endospore: none
(5) gram: negative
(6) oxidase: positive
(7) catalase: positive
(8) strictly aerobic The cited strain *Achromobacter xylosoxydans* DSM No. 2783 is deposited at the German Collection of Microorganisms (DSM), Gesellschaft fuer Biotechnologische Forschung mbH., Griesebachstrasse 8, 4300 Goettingen, Germany, under numbers DSM 2402 and DSM 2783.

The new strain *Achromobacter xylosoxydans* DSM 2783 was deposited on Nov. 18, 1983, in the German Collection Of Microorganisms (DSM), Gesellschaft fuer Biotechnologische Forschung mbH., Griesebachstrasse 8, 4300 Goettingen,Germany, under the designation or number DSM 2783. Such deposit of a culture of such new strain of microorganism in such depository affords permanence of the deposit and ready accessibility thereto by the public if a patent is granted, under conditions which assure (a) that access to the culture will be available during pendency of the patent application to one determined by the Commissioner to be entitled thereto under 37 C.F.R. 1.14 and 35 U.S.C. 112, and (b) that all restrictions on the availability to the public of the culture so deposited will be irrevocably removed upon the granting of the patent. The applicants or their assigns have provided assurance of permanent availability of the culture to the public through such depository.

The strains *Pseudomonas putida* NCIB 10521 and 8176 can readily be obtained at the National Collection of Industrial Bacteria, Torry Research Station 135 Abbey Road, Aberdeen AB98DC, Scotland.

The taxonomic description (to the extent presently known to us) of the strain *Pseudomonas putida* NCIB 8176 (ATCC 795; IFO BUCSAV 289), (*P. convexa*), (deposited as *P. mildenbergii*): Munoz, J. et al., J. Bact., 57 (1949), 269–278:
growth temperature tube, 37° C.
flagellar arrangement, lophotrichous
pigment, fluorescin
acid produced, glucose (maltose, sucrose and lactose were not produced)
gelatin liquefaction, negative
litmus milk, alkaline
nitrates reduced to nitrites, negative
hydrogen sulfide, negative
indole, negative
From Haynes, W. C., J. Bact., 81, (1961), 385–386:
Coccoid rods. Motile, possessing 1 to several polar flagella. Gram-negative.
Gelatin stab: Slow liquefaction. Surface growth bluish.
Agar colonies: Small, round, entire, umbonate, bluish white, spreading, becoming confluent, and forming an irregular, serrate, raised, mucoid, glistening, viscous to ropy steel blue growth. The medium becomes dark blue fluorescent. After 3 to 4 weeks, the pigment fades to blue green to green and eventually disappears.
Agar slant: Abundant, smooth or undulant, raised, moist, mucoid, glistening, viscous or ropy steel blue growth. The pigment gradually fades. The medium appears intensely blue to bluish violet and fluorescent.
Broth: Turbid with a grayish, viscid sediment and sometimes with a pellicle. The medium becomes light greenish yellow. Unpleasant odor.
Milk: Becomes weakly alkaline. No coagulation. Milk becomes blue violet to blue.
Potato: Luxuriant, slimy, glistening, raised, steel blue becoming dirty slate gray and then gray. The potato also becomes gray.
No gas from glucose.
Aerobic.
Optimal temperature, 18° to 22° C. Grows well at 37° C. but without pigment. Also grows well at 8° to 10° C.
Not pathogenic per os to rabbits, guinea pigs, or white mice.
Distinctive characters: Usually surface growth is blue and the growth medium becomes greenish yellow to blue or bluish violet. The blue pigment is readily soluble in water and glycerine, slightly soluble in alcohol, and insoluble in chloroform, benzene, amyl alcohol, carbon disulfide, ether, and xylene. It decolorizes upon standing, but quickly reoxidizes when the solution is shaken. Aqueous solutions of the pigment turn red in the presence of strong acids, turn green in the presence of strong alkalis, and become dirty violet in weakly alkaline solutions.
Source: Air
Habitat: Probably soil.
From Bartholomew, J. W., J. Gen. Microbiol., 3, (1949), 340–349, flagellation as reported in Bergey, (6th Ed.):
Motile, possessing polar flagella
From Lockwood, L. B., et al., J. Bact., 42 (1941), 51–61:
produces 2-ketogluconic acid The taxonomic description (to the extent presently known by us) of the strain *Pseudonomas putida* NCIB 10521 (Strain KB1):

contains thermostable NAD glycohydrolase From Kogut. M., et al., Biochem. J., 55 (1953), 800–811:
oxidizes succinate incompletely to alpha-ketoglutarate
washed suspensions of cells grown with succinate as the sole source of carbon oxidized citrate, isocitrate, cis-aconitate and alpha-ketoglutarate after a lag period. These adaptations were inhibited by irradiating the suspensions with ultraviolet light.
washed suspensions of cells grown with citrate as the sole source of carbon-oxidized succinate and alpha-ketoglutarate only after a lag period and irradiation of the suspension with ultraviolet light inhibited these adaptations.
Cell-free extrats of cells grown on a medium containing either succinate or citrate were found to contain the following enzymes: succinic dehydrogenase, fumarase, malic dehydrogenase, oxalo-acetic decarboxylase, aconitase, isocitric dehydrogenase and alpha-ketoglutaric oxidase.
Oxidation of tricarboxylic acid cycle intermediates by washed suspension of cells:

(Cup contents: 2.7 ml. containing 0.5 ml. of 0.066M phosphate buffer pH 7.4; 3.0 mg. dry wt. of cells in side bulb; and 5 μM substrate. 0.2 ml. 20% KOH in center well. Temp. 30°.)

| Growth substrate | Substrate for oxidation | | | | | | | | | |
|---|---|---|---|---|---|---|---|---|---|---|
| | Succinate | Fumarate | Malate | Oxalo-acetate | Pyruvate | Acetate | Citrate | cis-Aconitate | iso-Citrate | α-Keto-glutarate |
| Succinate | + | + | + | + | 0 | 0 | 0 | 0 | 0 | 0 |
| Fumarate | + | + | + | + | . | . | 0 | . | . | 0 |
| Malate | + | + | + | + | . | . | 0 | . | . | 0 |
| Acetate | 0 | 0 | . | . | + | + | 0 | . | . | 0 |
| Citrate | 0 | 0 | + | . | 0 | 0 | + | 0 | 0 | 0 |
| isoCitrate | 0 | 0 | + | . | . | . | + | + | + | 0 |
| α-Ketoglutarate | 0 | 0 | . | . | 0 | 0 | 0 | . | . | + |

+ = Substrate oxidized linearly from the moment of tipping.
0 = Substrate not linearly oxidized initially.

U.S. Pat. No. 4,738,924 contains information concerning *Achromobacter xylosoxydans* DSM 2783, *Pseudomonas putida* NCIB 10521 and *Pseudomonas putida* NCIB 8176. The pertinent portions of U.S. Pat. No. 4,738,924 concerning *Achromobacter xylosoxydans* DSM 2783, *Pseudomonas putida* NCIB 10521 and *Pseudomonas putida* NCIB 8176 are incorporated herein.

Both of the *Pseudomonas putida* strains are commercially available.

The following example explains the performance of the process according to the invention.

EXAMPLE (a) Production of the Starter Culture

A nutrient solution was produced from 5.19 g of dibasic sodium phosphate dihydrate, 2.00 g of monobasic potassium phosphate, 0.25 g of yeast extract, 1.00 g of nicotinic acid and 500 ml of water, and sterilized for 20 minutes at 120° C. After cooling to 30° C., a sterile concentrated trace element solution was added in such an amount that the following concentrations were reached in the culture medium:

| Calcium chloride dihydrate | 20 mg/l |
|---|---|
| Manganese (II) sulfate | 10 mg/l |
| Iron (II) sulfate heptahydrate | 5 mg/l |
| Cobalt (II) sulfate hexahydrate | 0.1 mg/l |
| Copper (II) sulfate pentahydrate | 0.1 mg/l |

-continued

| Zinc sulfate heptahydrate | 0.1 mg/l |
|---|---|
| Sodium molybdate dihydrate | 0.1 mg/l |

The culture medium was inoculated with *Achromobacter xylosoxydans* DSM 2783 and cultured for 24 hours at 30° C. and pH 7.

(b) Production of 6-hydroxynicotinic acid 12 liters of water, 90 g of nicotinic acid, 19.44 g of sodium hydroxide, 90 g of yeast extract, 12 g of potassium sulfate, 9.6 g of magnesium chloride hexahydrate, 1.92 g of calcium chloride, 2.4 ml of polypropylene glycol 2000, 180 g of L-glutamic acid and 300 g of glucose were dissolved in a 20-liter fermenter with stirrer, aeration and pH adjustment, and sterilized for 30 minutes at 121° C. After cooling to 30° C., the starter culture was added and cultured with air feed and stirring at pH 7 for 10 hours. After this period, the nicotinic acid concentration had dropped from 7.5 g/l to 2 g/l (HPLC determination) and the biomass concentration had risen to 10 g/l (dry weight). At this moment, a beginning was made with the continuous addition of a solution of 1.13 kg of nicotinic acid and 0.365 kg of sodium hydroxide in 3.00 liters of water sterilized for 20 minutes at 121° C. and the rate of addition was adjusted so that the nicotine concentration in the fermenter during the addition was between 1 g/l and 9 g/l. The addition was ended after 11 hours, the glutamic acid and glucose were completely consumed and the biomass concentration had increased to 15 g/l (dry weight). After another 4 hours, i.e., a total of 25 hours after inoculation, the fermentation was terminated. The final concentration of 6-hydroxynicotinic acid was 74 g/l, which corresponds to a practically quantitative conversion of nicotinic acid to 6-hydroxynicotinic acid. Working up took place as described in Swiss Patent No. 658,866 (Examples 1 and 3).

What is claimed is:

1. Process for the production of 6-hydroxynicotinic acid by microbiological hydroxylation of nicotinic acid under aerobic conditions, characterized in that nicotinic acid or a soluble salt of nicotinic acid or a solution containing nicotinic acid is added continuously or by portions to a starter culture of the microorganism, in that the microorganism is selected from the group consisting of *Achromobacter xylosoxydans* of strain DSM 2783, *Pseudomonas putida* of strain NCIB 10521 and *Pseudomonas putida* of strain NCIB 8176, and in that the nicotinic acid concentration in the culture during the period of addition is always greater than zero and at least remains substantially below the concentration, above which a growth inhibition of the microorganisms occurs, until the formed 6-hydroxynicotinic acid inhibits further growth, so that the multiplication of the microorganism and the formation of the 6-hydroxynicotinic acid take place in the same process step.

2. Process according to claim 1 wherein the microorganism is *Achromobacter xylosoxydans* of strain DSM 2783.

3. Process according to claim 1 wherein the microorganism is *Pseudomonas putida* of strain NCIB 10521.

4. Process according to claim 1 wherein the microorganism is *Pseudomonas putida* of strain NCIB 8176.

* * * * *